Nov. 28, 1933. S. R. WESTON Plant Pat. 83
VIOLA
Filed May 15, 1933
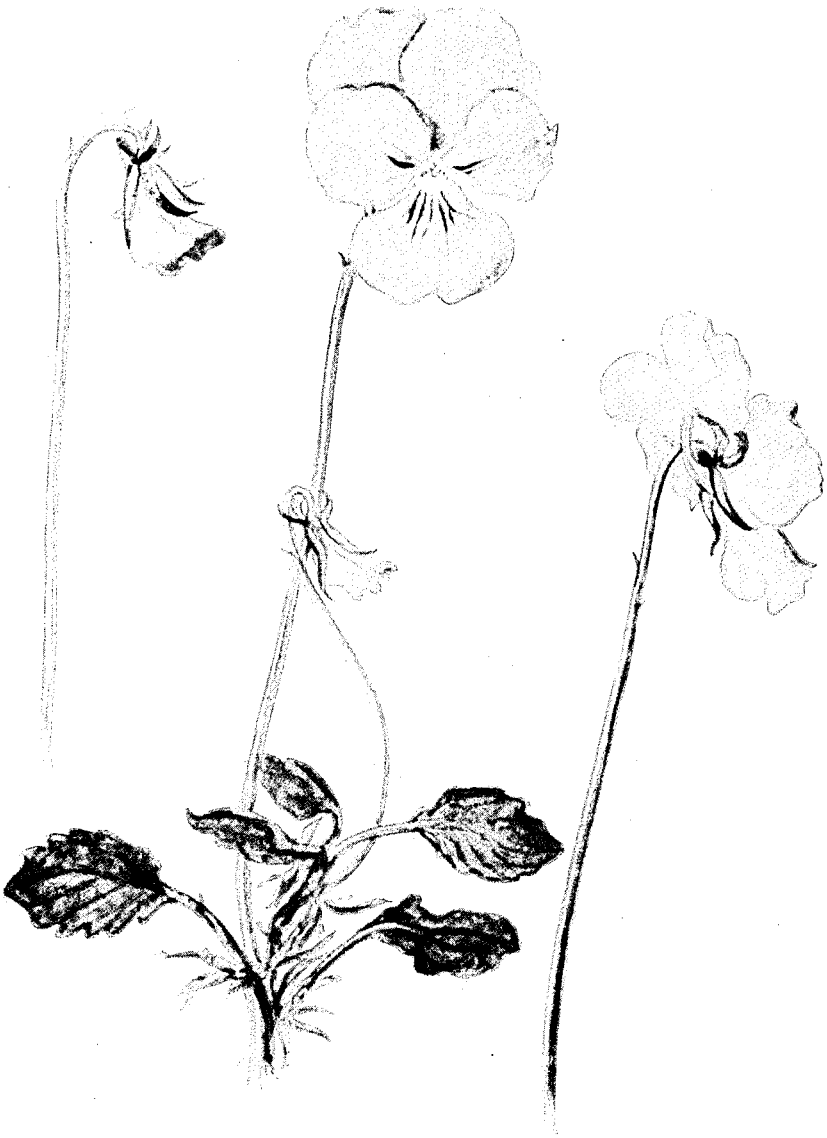
INVENTOR
Stuart R Weston.
By Orville M Kile
Plant Patent Agent Patented Nov. 28, 1933

UNITED STATES PATENT OFFICE

83

VIOLA

Stuart R. Weston, Marcy, N. Y.

Application May 15, 1933. Serial No. 671,205

1 Claim. (Cl. 47—60)

My invention relates to improvements in viola plants of the type grown commercially by florists. The object of my invention is to provide a new and distinct variety of the type of viola plant mentioned, having desirable and useful qualities not found in any other existing variety.

More specifically stated, my invention consists in the production of a new and distinct variety of viola having larger flowers and longer and heavier flower stems, combined with more compact foliage and having desirable color and odor qualities as well as advantageous habits of growth.

This new variety originated as a seedling. One of the parents is the well-known variety Jersey Gem, the other is unknown. The first plant of this new variety attracted my attention in the summer of 1929. I gave it special care and attention and it bloomed in the summer of 1930. I propagated this variety by asexual means, since it apparently produces no seed or at least none have ever germinated around the original plant.

The accompanying illustration shows (in the originals) the fully opened flowers and two buds all in natural size and color as grown in a greenhouse in the month of April. The following is a detailed description;

The plant has rather sparse foliage and the leaves have a noticeably smaller size than the well-known variety Jersey Gem. The plant probably does not mature seed, since it has been planted next to various other violas and pansies but I have never been able to secure a seedling from it. The older flowering growth gradually dies away and the new shoots which constantly appear keep the plant in continuous bloom from early spring until late fall when the flower buds are killed by freezing. Frosts do not stop the blooming. This continues until the ground freezes.

The plant readily adapts itself to greenhouse forcing.

*The foliage.*—The individual leaves are relatively small and have exceptionally long petioles. Typical leaves measure 1 inch to 1¼ inches in length while the petioles may be as long or longer. The leaves are decidedly notched, with 3 to 5 notches or protrusions on each edge of the leaf, in addition to the large protrusion which constitutes the tip of the leaf.

The stems are strong and heavy and ordinarily 5 to 6 inches in length. Each stem bears two very small rudimentary leaflets about one inch below the blossom. Although arranged on opposite sides of the stem, one of the leaflets is located considerably above the other.

The color of both foliage and flower stems is approximately "forest green."

The flowers measure 1¾ to 2 inches across the face in their longest dimension. The sepals are 5 in number, long and slender and of forest green color. The flower is of typical viola form. The lighter portions of the upper surface of the petals are approximately "Hortense violet" in color (Plate XI of Ridgway's Color Standards and Nomenclature) and the darker portions are approximately "plemora violet" (Plate XXV). The under side of the petals is approximately "mauve" (Plate XXV), except that toward their points of attachment the lower three petals become quite light.

The "eye" of the flower is approximately "lemon chrome" in color (Plate IV).

The lower petal has generally 5, although sometimes 6, deep purple lines or veins radiating from the eye. Each of the two side petals has one or sometimes two similar dark or deep purple lines, but the upper two petals have no such lines.

The petals when viewed from the edge have a crinkled or waved effect.

*The odor.*—While the odor is similar to that of Jersey Gem it is present in notably larger quantity.

The principal characteristics which I believe distinguish my new variety from all other violas and particularly from Jersey Gem are;

1. The large size of its flowers.
2. The small size and distinctive shape of its leaves.
3. The colorings and markings of its flowers as above described.
4. The intensity and volume of its odor.
5. The strength, size and length of its flower stems.
6. Its apparent inability to produce viable seeds.
7. Its resistance to frosts and its long flowering season.

Having thus disclosed my invention, I claim:

The variety of viola herein shown and described, characterized particularly by its small and compact foliage, its large flowers borne on stout, long stems and having distinctive violet to mauve-colored petals with lemon-chrome "eye" and dark purple lines radiating therefrom, also having intensely fragrant odor, and the plant being further characterized by its long flowering season and its resistance to cold weather.

STUART R. WESTON.